United States Patent
Kojima et al.

(10) Patent No.: US 10,031,089 B2
(45) Date of Patent: Jul. 24, 2018

(54) METHOD FOR EVALUATING INTERNAL STRESS OF SILICON CARBIDE MONOCRYSTALLINE WAFER AND METHOD FOR PREDICTING WARPAGE IN SILICONE CARBIDE MONOCRYSTALLINE WAFER

(71) Applicant: NIPPON STEEL & SUMIKIN MATERIALS CO., LTD., Saitama (JP)

(72) Inventors: Kiyoshi Kojima, Saitama (JP); Masashi Nakabayashi, Saitama (JP); Kota Shimomura, Saitama (JP); Yukio Nagahata, Saitama (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 15/023,254

(22) PCT Filed: May 30, 2014

(86) PCT No.: PCT/JP2014/064525
§ 371 (c)(1),
(2) Date: Mar. 18, 2016

(87) PCT Pub. No.: WO2015/040895
PCT Pub. Date: Mar. 26, 2015

(65) Prior Publication Data
US 2016/0231256 A1 Aug. 11, 2016

(30) Foreign Application Priority Data
Sep. 20, 2013 (JP) .................................. 2013-195011

(51) Int. Cl.
*G01N 21/95* (2006.01)
*G01N 21/65* (2006.01)
(Continued)

(52) U.S. Cl.
CPC ......... *G01N 21/9505* (2013.01); *C30B 23/00* (2013.01); *C30B 29/36* (2013.01);
(Continued)

(58) Field of Classification Search
CPC ....... G01N 21/9505; G01N 21/65; G01L 1/24
See application file for complete search history.

(56) References Cited

U.S. PATENT DOCUMENTS

| | | |
|---|---|---|
| 2004/0134418 A1 | 7/2004 | Hirooka |
| 2006/0038980 A1* | 2/2006 | Naka .................. G01N 21/65 356/73 |

(Continued)

FOREIGN PATENT DOCUMENTS

| | | |
|---|---|---|
| JP | 1179896 | 3/1999 |
| JP | 2004131328 | 4/2004 |

(Continued)

OTHER PUBLICATIONS

English translation of Hiroyuki et al. (JPH1179896), Mar. 3, 1999.*
(Continued)

*Primary Examiner* — Dominic J Bologna
(74) *Attorney, Agent, or Firm* — Hunton Andrews Kurth LLP

(57) ABSTRACT

Provided are a method of evaluating an internal stress of a silicon carbide (SiC) single crystal wafer and a method of predicting warpage of the SiC single crystal wafer after completion of polishing by evaluating the internal stress of the wafer. Wavenumber shift amounts of Raman-scattered light are measured at two points within a surface of the SiC single crystal wafer, and the internal stress is evaluated through use of a difference between the wavenumber shift amounts. Also provided is a method of predicting warpage of a silicon carbide single crystal wafer in advance, the silicon carbide single crystal wafer being produced by
(Continued)

sublimation-recrystallization method, the method including predicting warpage of a SiC single crystal wafer through use of the evaluation indicator.

4 Claims, 4 Drawing Sheets

(51) Int. Cl.
*G01L 1/24* (2006.01)
*C30B 23/00* (2006.01)
*C30B 29/36* (2006.01)
*C30B 33/00* (2006.01)
*H01L 21/66* (2006.01)

(52) U.S. Cl.
CPC ............... *C30B 33/00* (2013.01); *G01L 1/24* (2013.01); *G01N 21/65* (2013.01); *H01L 22/12* (2013.01); *G01N 2201/06113* (2013.01)

(56) References Cited

U.S. PATENT DOCUMENTS

| | | | |
|---|---|---|---|
| 2012/0248455 A1* | 10/2012 | Van Gestel | H01L 21/0237 257/75 |
| 2012/0280355 A1* | 11/2012 | Akiyama | H01L 21/76254 257/507 |
| 2013/0217212 A1* | 8/2013 | Yang | H01L 21/02381 438/478 |
| 2014/0261998 A1* | 9/2014 | Veerasamy | B82Y 30/00 156/247 |
| 2015/0062561 A1* | 3/2015 | Yao | G01N 21/65 356/72 |

FOREIGN PATENT DOCUMENTS

| | | |
|---|---|---|
| JP | 2005093519 | 4/2005 |
| JP | 2005 314167 A | 11/2005 |
| JP | 2006290705 | 10/2006 |
| JP | 2005 147607 A | 6/2007 |
| JP | 2008227534 | 9/2008 |
| JP | 2011138932 | 7/2011 |

OTHER PUBLICATIONS

English translatino of Masashi et al. JP 2005314167, Nov. 10, 2005.*
Tairov, Yu. M. and Tsvetkov, V. F., General Principles of Growing Large-Size Single Crystals of Various Silicon Carbide Polytypes, Journal of Crystal Growth, 1981, pp. 146-150, vol. 52, North-Holland Publishing Company.
Burk, A. A. et al., SiC Epitaxial Layer Growth in a 6x150 mm Warm-Mall Planetary Reactor, Materials Science Forum, 2012, pp. 75-80, vol. 717-720, 2012 Trans Tech Publications, Switzerland.
Nakashima, S. and Harima, H., Ramen Investigation of SiC Polytypes, Physica Status Solidi. A. Applied Research, 1997, p. 39, 51, vol. 162, Germany.
English Translation of the Written Opinion of the International Searching Authority dated Sep. 2, 2014 issued in International Application No. PCT/JP2014/064525.
Supplementary European Search Report for Application No. EP 14 84 5966, dated Apr. 18, 2017.
Mermoux, M., et al., Raman imaging analysis of SiC wafers, Materials Science Forum, vol. 433-436, Sep. 15, 2003, pp. 353-356.
Olego, Diego, et al., Pressure dependence of the optical phonons and transverse effective charge in 3C-SiC, Physical Review B, vol. 25, No. 6, pp. 3878-3888, Mar. 15, 1982, The American Physical Society.

* cited by examiner

METHOD FOR EVALUATING INTERNAL STRESS OF SILICON CARBIDE MONOCRYSTALLINE WAFER AND METHOD FOR PREDICTING WARPAGE IN SILICONE CARBIDE MONOCRYSTALLINE WAFER

CROSS-REFERENCE TO RELATED APPLICATION(S)

This application is a national stage application of International Application No. PCT/JP2014/064525, filed May 30, 2014, which is incorporated herein by reference in its entirety, and which claims priority to Japanese Application No. 2013-195011, filed Sep. 20, 2013.

TECHNICAL FIELD

The present invention relates to a method of evaluating an internal stress of a silicon carbide single crystal wafer, and a method of predicting warpage of a silicon carbide single crystal wafer.

BACKGROUND ART

Silicon carbide (SiC) is a wide-bandgap semiconductor having a wide forbidden band of from 2.2 eV to 3.3 eV, and due to excellent physical and chemical characteristics thereof, research and development of SiC as an environmentally-resistant semiconductor material have been carried out. Particularly in recent years, SiC is drawing attention as a material for a short-wavelength optical device configured to emit blue light to ultraviolet light, a high-frequency electronic device, and a high-breakdown-voltage and high-output electronic device, and the research and development of SiC are becoming active. However, SiC is considered to be difficult to produce a good-quality single crystal having a large diameter, which has hitherto prevented a SiC device from being put into practical use.

Hitherto, on a scale of a research laboratory, for example, a sublimation-recrystallization method (Lely method) has been used to obtain a SiC single crystal having a size capable of manufacturing a semiconductor element. However, according to this method, the area of a single crystal to be obtained is small, and it is not easy to control the dimensions, shape, crystal polymorph (polytype), and concentration of impurity carriers. Meanwhile, chemical vapor deposition (CVD) has also been used to grow a cubic SiC single crystal through heteroepitaxial growth on a foreign substrate of silicon (Si) or the like. In this method, a single crystal having a large area is obtained, but only a SiC single crystal containing a large number of defects ($\approx 10^7/cm^2$) can be grown due to the lattice mismatch between SiC and Si of about 20%, with the result that a high-quality SiC single crystal has not been obtained.

In order to solve the above-mentioned problems, there has been proposed a modified Lely method involving performing sublimation-recrystallization through use of a SiC single crystal wafer as a seed crystal (see Non Patent Literature 1). When the modified Lely method is used, a SiC single crystal can be grown while controlling the crystal polymorph (6H-type, 4H-type, 15R-type, etc.), shape, carrier type, and concentration of the SiC single crystal. It should be noted that, among 200 or more crystal polymorphs (polytypes) of SiC, a 4H polytype is considered to be most excellent in terms of the productivity of a crystal and the performance of an electronic device, and hence most of SiC single crystals that have been commercially produced are of the 4H-type. Further, a single crystal ingot is grown so as to have n-type conductivity in most cases because nitrogen is easy to handle as a dopant. It should be noted that a crystal having a high resistivity, which is substantially free of a dopant element, has also been produced in the application to communication devices.

In order to use a SiC single crystal ingot as a SiC wafer for manufacturing a semiconductor device, it is necessary to process the SiC single crystal ingot produced by a method such as the above-mentioned modified Lely method into a wafer shape through the process mainly involving cutting and polishing. That is, a SiC single crystal wafer having a thin plate shape, which is cut by a method such as a wire saw so that a desired crystal surface is exposed, is subjected to mirror polishing processing through a polishing process substantially similar to a method that is generally performed in other semiconductor materials such as silicon, and various electronic devices are manufactured through use of the SiC single crystal wafer thus produced.

Currently, a SiC single crystal wafer having a diameter of from 51 mm (2 inches) to 100 mm is cut out from a SiC single crystal produced by the modified Lely method and is used for manufacturing devices in the fields of power electronics and the like. Further, the success of the development of a wafer having a diameter of 150 mm has also been reported (see Non Patent Literature 2), and thus the full-scale commercial manufacturing of devices using a wafer having a diameter of 100 mm or 150 mm is being realized.

Incidentally, in general, the flatness of a wafer expressed as so-called "warpage" is considered to be very important in terms of a device step. This is because, in a wafer having poor flatness, that is, having large warpage, a part within a wafer surface becomes out of focus in an exposure process (lithograph process), with the result that a clear mask image is not formed. Needless to say, the out-of-focus phenomenon has a larger effect as a circuit is finer.

If the warpage of a product wafer after polishing can be predicted before the completion of the polishing step, steps can be selected, for example, as follows: a wafer is polished after selecting an application based on the value of warpage (polishing specifications vary depending on the kind of a device inmost cases); a wafer that has been found to be unable to be formed into a product based on the magnitude of warpage is not subjected to the polishing step; or a wafer is subjected to annealing treatment at high temperature and classified into the application in which a dislocation density is allowed. With this, a wafer can be efficiently formed into a product, and simultaneously, the waste of the expensive polishing step is cut to decrease cost. Therefore, the prediction of warpage is very important from the industrial viewpoint.

The warpage of a SiC single crystal wafer is generally determined based on the following three factors: (i) internal stress of a crystal; (ii) accuracy of cutting and processing residual strain on front and back surfaces of a wafer; and (iii) removal of residual strain on front and back surfaces in a polishing step and the process thereof. The factor (i) is determined by the conditions of crystal growth and the heat treatment to be conducted thereafter. The factor (ii) is determined by the accuracy of the motions of a wire and a blade, and the processing strain applied to a surface in a cutting step. A change in warpage caused by the factor (iii) is generally called a Twyman's effect, and in this case, a wafer is warped so that a surface having large strain is projected. That is, the warpage of a wafer reaches the warpage of a product wafer after the completion of final polishing through different courses during the process, depending on the growth conditions, the accuracy of the cutting step and the polishing step, and the contents thereof. As a result, the value of the magnitude of the warpage of the wafer in the polishing step is not matched with that of the magnitude of the warpage of the wafer after the completion of final polishing, and in addition, the tendency of a change in warpage in the steps is not uniform. Thus, hitherto, there has been no technology of predicting the warpage of a wafer before the completion of polishing.

Meanwhile, as means for reducing the warpage amount of a wafer, for example, the following methods have been considered. In Patent Literature 1, there has been reported a technology involving subjecting a wafer cut out from a SiC single crystal ingot to annealing treatment at a temperature of 1,300° C. or more and 2,000° C. or less so as to remove a processing residual stress caused by grinding and cutting of the ingot, thereby reducing the warpage amount of a wafer. Further, in Patent Literature 2, there has been reported a technology involving annealing an ingot or a wafer of a SiC single crystal at a temperature of more than 2,000° C. and 2,800° C. or less in an atmosphere of noncorrosive gas containing carbon and hydrogen or an atmosphere in which argon and helium are mixed with the noncorrosive gas, so as to relieve the internal stress of the ingot or the wafer, thereby preventing cracking and cracks during processing of the ingot or in a device process of the wafer. Further, in Patent Literature 3, there has been reported a technology involving subjecting a wafer cut out from a SiC single crystal ingot to heat treatment at 800° C. or more and 2,400° C. while pressurizing the wafer at 10 MPa or more and 0.5 MPa or less, thereby setting the radius of curvature of the wafer to 35 m or more. In Patent Literature 4, there has been proposed a polishing and surface-finishing technology of reducing warpage, and there has also been disclosed a technology involving removing a processing altered layer formed by mechanical flattening processing or cutting processing by vapor-phase etching, thereby eliminating the warpage of a SiC wafer.

Patent Literature 1, 2, or 3 is considered to be effective for relieving the internal stress of a grown crystal. However, when atoms are rearranged by applying a thermal load of more than 2,000° C. from outside to a SiC single crystal, a new crystal defect may be caused. An increase in dislocation density of a crystal after annealing in Examples of Patent Literature 3 indicates the above-mentioned phenomenon. Further, what can be commonly said about Patent Literature 4 as well as Patent Literatures 1, 2, and 3 is that those technologies are not for predicting the warpage of a wafer after polishing. In the industrial-scale production, it is impossible to set the warpage of all wafers to a value close to 0, and even when a production technology of reducing the warpage is available, the evaluation technology of predicting the warpage is still important.

CITATION LIST

Patent Literature

[PTL 1] JP 2004-131328 A
[PTL 2] JP 2006-290705 A
[PTL 3] JP 2005-93519 A
[PTL 4] JP 2008-227534 A

Non Patent Literature

[NPL 1] Yu. M. Tairov and V. F. Tsvetkov, Journal of Crystal Growth, vols. 52 (1981) pp. 146-150

[NPL 2] A. A. Burk et al., Mater. Sci. Forum, 717-720, (2012) pp 75-80

SUMMARY OF INVENTION

Technical Problem

As described above, it is industrially very important to predict the warpage of a SiC wafer, but hitherto the technology of predicting warpage has not been established.

The present invention has been made so as to solve the above-mentioned problems, and it is an object of the present invention to evaluate the internal stress of a wafer and predict, before the completion of a polishing step, a value of the warpage of a SiC single crystal product wafer after the completion of polishing.

Solution to Problem

In order to solve the above-mentioned problems, the inventors of the present invention have worked on the elucidation of the warpage phenomenon based on the viewpoint of the above-mentioned three major factors of the warpage of a SiC wafer. As a result, surprisingly, the inventors of the present invention have found that the warpage amount of the wafer after the completion of polishing produced under known cutting and polishing conditions with certain high accuracy can be expressed as a function of an internal stress value of a crystal. That is, when the internal stress of the crystal is measured, the warpage of the wafer can be predicted. However, there is a problem regarding how to evaluate the internal stress. As a method of evaluating an internal stress, for example, accurate measurement of a lattice constant with an X-ray has been generally known. However, in order to perform this measurement, there are problems in that an expensive facility and high-degree skill are required, and the measurement time is long. Thus, the accurate measurement is not suitable for inspection in mass-production factories. In view of the foregoing, the inventors of the present invention have found a method of evaluating an internal stress of a SiC wafer simply within a short period of time, thereby achieving the present invention.

Specifically, the present invention includes the following configuration.
(1) A method of evaluating an internal stress of a silicon carbide single crystal wafer, the silicon carbide single crystal wafer cut out from the silicon carbide single crystal ingot being produced by a sublimation-recrystallization method, through use of a difference between Raman shift values measured at two points within a principal surface of the silicon carbide single crystal wafer.
(2) A method of evaluating an internal stress of a silicon carbide single crystal wafer according to Item (1), the method including using a Raman shift difference (A−B) between a Raman shift value (A) measured at a center and a Raman shift value (B) measured in an outer peripheral portion.
(3) A method of predicting warpage of a silicon carbide single crystal wafer in advance, the silicon carbide single crystal wafer being produced by a sublimation-recrystallization method,
the method including estimating warpage of the silicon carbide single crystal wafer after completion of a polishing step through use of a difference between Raman shift values at two points within any one of a front surface and a back surface, which is measured before final polishing in obtaining the silicon carbide single crystal wafer.

(4) A method of predicting warpage of a silicon carbide single crystal wafer according to Item (3), the method including using a difference between Raman shift values measured at two points within any one of a front surface and a back surface of a single crystal thin plate obtained by slicing a silicon carbide single crystal ingot obtained by the sublimation-crystallization method.

(5) A method of predicting warpage of a silicon carbide single crystal wafer according to item (3) or (4), the method including: determining, in advance, a relationship between the difference between the Raman shift values and the warpage of the silicon carbide single crystal wafer; and predicting, based on an obtained relational expression, the warpage of the silicon carbide single crystal wafer from the difference between the Raman shift values.

Advantageous Effects of Invention

When the evaluation method according to one embodiment of the present invention is used, the warpage value of the wafer after the completion of polishing can be predicted in advance. Therefore, a wafer obtained by slicing a silicon carbide single crystal ingot can be efficiently formed into a product, and the production cost can also be reduced.

DESCRIPTION OF EMBODIMENTS

Figure 1:
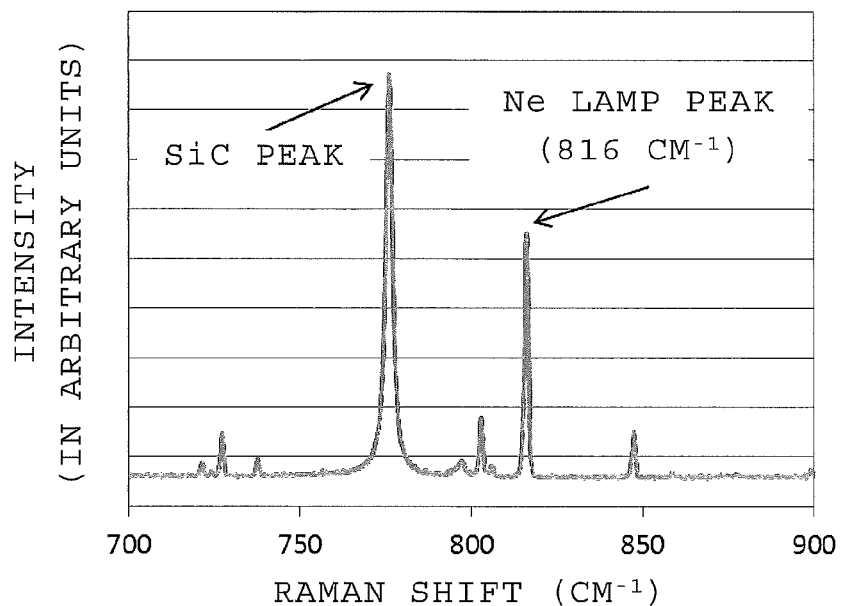
FIG. 1 is an example of Raman-scattered light measurement data on a SiC wafer.
Figure 2:
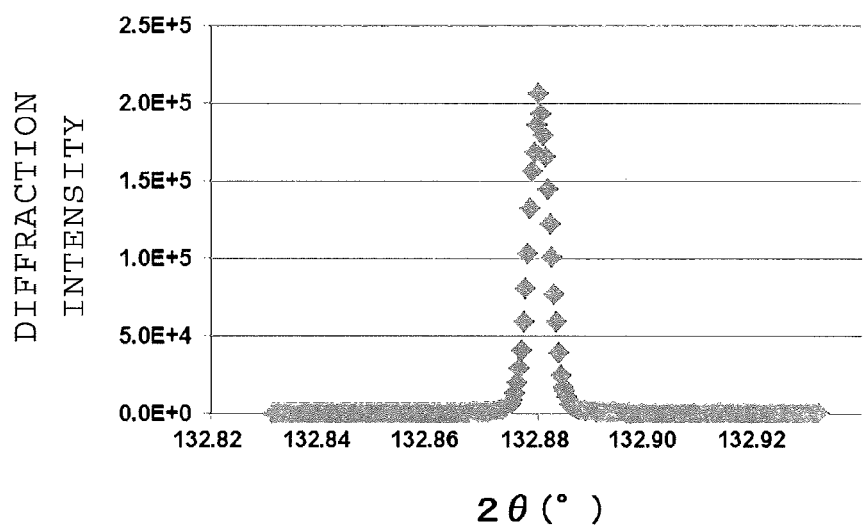
FIG. 2 is an example of {0008} X-ray diffraction data on SiC.

Now, the present invention is described in detail.

As a procedure for measuring an internal stress relatively simply within a short period of time, there is known a method using a change in peak wavenumber of Raman-scattered light, a so-called Raman shift. It is a well-known fact that, when a crystal has an internal stress, the distance between atoms changes, and along with this, the peak wavenumber of Raman-scattered light shifts. That is, the peak wavenumber shifts to a high wavenumber side in a compressive stress, and the peak wavenumber shifts to a low wavenumber side in a tensile stress.

However, a SiC single crystal has a strong covalent bond, and a Raman shift caused by a stress difference is very small and is also influenced, for example, by a wavenumber drift of calibration lamp light. Therefore, even when the Raman shift can be measured, it is difficult to obtain a value withstanding a practical level. In view of the foregoing, the inventors of the present invention have found that when Raman shifts are measured at two points within a wafer principal surface, and a difference therebetween (hereinafter referred to as "Raman index") is determined, data capable of evaluating an internal stress of the wafer is obtained while the influence of a calibration drift or the like is avoided. That is, in general, in accurate Raman measurement, a change in environment significantly influences a measurement value (a typical example thereof is a drift of a wavelength peak of a Ne lamp for calibration as described above). However, when Raman shifts are measured at two points within the wafer surface and a difference therebetween is determined, the internal stress of the wafer can be evaluated with the influence of external disturbance such as a drift of a Ne lamp being excluded.

Herein, the internal stress of a silicon carbide single crystal wafer produced by a sublimation-recrystallization method (hereinafter sometimes referred to simply as "wafer") is distributed in a concentric fashion. This is considered as described below. A SiC single crystal ingot obtained by the sublimation-recrystallization method is generally produced in a temperature gradient environment that is symmetric with respect to a center axis, and hence the internal stress thereof is also symmetric with respect to the center axis with a stress being graded from the center to an outer peripheral portion. Thus, Raman shifts are basically measured at two points on the center side and the circumferential side, and a difference therebetween is determined. For example, it is sufficient that the second point for measurement be defined in a radial direction based on the center of the wafer. When a plurality of measurement points are defined, and a Raman index thereof is analyzed, the stress distribution within a surface can also be evaluated. In general, the internal stress becomes minimum or maximum at the center and the outer periphery of the wafer, and hence the magnitude of the internal stress of the wafer can be expressed most simply and accurately through use of a difference (A−B) between a Raman shift value (A) measured at the center and a Raman shift value (B) measured in the outer peripheral portion.

There is no particular limitation on the position of the measurement point in the outer peripheral portion. As the measurement position is as close as possible to an edge, the Raman index increases. On the other hand, the vicinity of the edge is a so-called edge exclusion region, and there is a problem of crystal quality in some cases. In addition, the influence of processing residual strain caused by chamfering processing cannot be ignored. Therefore, as the measurement point in the outer peripheral portion, a position closer to the center by about from 1 mm to 10 mm with respect to the edge of the wafer is appropriate. The Raman index changes depending on the position of the measurement point, and hence it is desired that the position of the measurement point be fixed in determining the Raman index. The warpage value of a wafer after the completion of polishing (product wafer) can be predicted through use of the value of (A−B) defined as described above. That is, when the relationship between the difference between Raman shift values and the warpage of the wafer is determined in advance, the warpage of the wafer can be predicted from the difference between the Raman shift values based on the obtained relational expression.

The warpage of a wafer is expressed by a difference in height within a wafer surface, and there are some methods for the measurement. In the present invention, the warpage of the wafer refers to a value measured with an optical interferometer. The optical interferometer generally irradiates the wafer surface with coherent light so that the light is reflected therefrom, and observes a difference in height within the wafer surface as a phase shift of the reflected light. Through use of the optical interferometer, the height in a vertical direction with respect to a reference plane within the wafer surface of a SiC single crystal excluding a region of 2 mm from a peripheral portion, which is placed on the reference plane without any binding force, is measured, and a difference between the maximum point and the minimum point of the height is defined as warpage.

The Raman measurement for predicting warpage can be performed in any stage during wafer processing. In general, when a SiC single crystal wafer is obtained, a cutting step involving slicing a SiC single crystal ingot to cut out a SiC single crystal (single crystal thin plate) having a thin plate shape is performed, and then, for example, the SiC single crystal is subjected to a polishing step including various polishing treatments, such as lapping for removing the unevenness of the surface, diamond polishing for increasing the smoothness of the surface, and chemical mechanical polishing (CMP) for removing processing strain on the wafer surface. Therefore, in order to predict the warpage of the wafer after the completion of the polishing step in advance, it is sufficient that the warpage be predicted before final polishing in the polishing step of finishing the wafer (the kind of the final polishing varies depending on the quality required of the product wafer and further varies between a front surface and a back surface (Si surface, C surface) in some cases). It is most desired that the warpage be measured at two points within any one of the front and back surfaces after cutting from the SiC single crystal ingot, that is, in a state of the single crystal thin plate not subjected to polishing processing, because the degree of freedom of selecting subsequent steps becomes maximum. It should be noted that there is no particular limitation on the device and conditions for the Raman measurement, and it is desired that the resolution be about +/−0.05 cm$^{-1}$. There is no particular limitation on the light source, and a green laser having a wavelength of 532 nm is generally used.

Further, as described above, the required thickness and the kind of the final polishing treatment of the SiC single crystal wafer may vary depending on the application and the like. Therefore, when the relational expression between the difference between the Raman shift values and the warpage of the SiC single crystal wafer is obtained, it is desired that each relational expression be prepared in accordance with a combination of each polishing condition on the front and back surfaces (Si surface, C surface) and the thickness of the SiC single crystal wafer to be obtained.

EXAMPLES

Now, the present invention is described specifically by way of Examples.

Example 1

Two SiC single crystal wafers (wafer Nos. 11 and 12) each having a diameter of 100 mm and including a <0001> surface as a principal surface, the SiC single crystal wafers being produced by a sublimation-recrystallization method, were measured for a Raman index, and further an internal stress of each of the wafers was also measured by an X-ray diffraction procedure. The front and back surfaces of the wafer were finally polished with a diamond slurry having an average particle diameter of 0.5 μm so that the wafer was mirror-finished and had a thickness of about 2.3 mm after polishing. Such a thick wafer was used in order to perform accurate measurement while avoiding stress relief by deformation.

The measurement of a Raman index was performed under the following conditions. A green laser of 532 nm was used as a light source for the Raman measurement, and a spot of φ2 μm of a sample surface was irradiated with the green laser. In one measurement portion, a total of 72 points (8 rows and 9 columns) were irradiated with the measurement light at a spot interval of 10 μm, and an average value thereof was defined as data on the measurement portion. In one wafer, Raman-scattered light of SiC was measured in two portions, the center of one measurement portion being the center of the wafer, the center of the other measurement portion being a position away from an edge (outer periphery) of the wafer by 2 mm (position away from the edge by 2 mm toward the center of the wafer). Then, a difference (value at the center−value at the position away from the outer periphery by 2 mm) between wavenumbers (inverse numbers of a wavelength) of Raman-scattered light peaks of SiC is defined as a Raman index. A measurement example of Raman-scattered light is shown in FIG. 1. A peak at 816 cm$^{-1}$ of a Ne lamp was used for calibration of scattered-light measurement. The measurement time was about from 4 minutes to 6 minutes per wafer (two measurement portions). It should be noted that the Raman measurement was performed in the following Examples 2 and 3 as well as Example 1 through use of a Raman spectrometer (NRS-7100 manufactured by JASCO Corporation, resolution: ±0.05 cm$^{-1}$).

X-ray diffraction (hereinafter referred to as "XRD") was performed under the following conditions. An X-ray source is a rotary anticathode (copper target), and a rated output is 18 kW. The incidence and detection of an X-ray were performed in parallel with a <11-20> direction of the wafer. Accurate X-ray diffraction was performed on three reflection surfaces of {00012}, {11-28}, and {1-1010} in two portions: the center of the wafer to be measured and the position away from the edge by 2 mm in the same way as in the measurement points of the Raman measurement, and lattice strain of three principal surfaces of SiC, that is, {0001}, {11-20}, and {1-100} was calculated. The modulus of elasticity of SiC was set to 433 GPa in a <0001> direction and to 474 GPa in a direction orthogonal to the <0001> direction, and an internal stress value of the wafer was derived from the above-mentioned strain value. From the relationship between the incident direction of the X-ray and the crystal orientation, for example, the stress in the crystal orientation <1-100> direction corresponds to the circumferential stress of the wafer. Similarly, the <0001> is the thickness direction, and the <11-20> is the radial direction. In order to perform diffraction measurement of the above-mentioned three orientations in two portions of one wafer, about 6 hours were required. It should be noted that the above-mentioned {00012} represents {0, 0, 0, 12}, and the above-mentioned {1-1010} represents {1, −1, 0, 10}.

Figure 3:
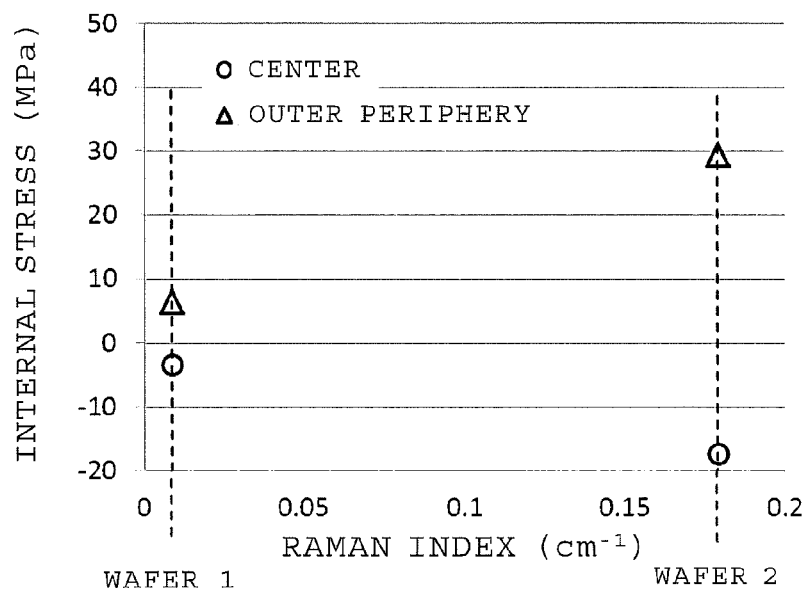
FIG. 3 is a graph for showing a relationship between a Raman index and an internal stress.

The measurement results of the Raman index and the internal stress are shown in Table 1 and FIG. 3. The internal stress was largest in the circumferential direction and 10 times or more as large as the stress in the other directions. Therefore, only the stress in the circumferential direction is shown in Table 1.

As shown in Table 1 and FIG. 3, although the Raman index does not include information on the distribution and direction of a stress, it is understood that the entire magnitude of the internal stress of the wafer can be evaluated based on the Raman index because the Raman index and the internal stress have a correspondence relationship. It should be noted that both the Raman measurement and the XRD were performed on both the Si surface and the C surface of the wafer, and in Table 1 and FIG. 3, data on the Si surface is used. The difference in Raman index between the Si surface and the C surface fell within an error range, and the tendency dependent on the surface orientation was not observed. In the XRD, the difference in circumferential stress depending on the surface orientation was less than 1%, which was not a significant difference.

TABLE 1

| Wafer No. | Measurement point | Raman shift | Raman index | Internal stress value obtained by XRD (circumferential direction, MPa) |
|---|---|---|---|---|
| 11 | Center | 776.6694 | 0.0083 | −3.4 |
|  | Outer periphery | 776.6611 |  | 6.5 |
| 12 | Center | 776.4989 | 0.1788 | −17.3 |
|  | Outer periphery | 776.3201 |  | 29.5 |

Example 2

Next, as Example 2, sixteen 4-inch wafers (single crystal thin plates) each having a thickness of 500 µm cut from a plurality of SiC single crystal ingots obtained by a sublimation-recrystallization method were prepared and measured for a Raman index. The Raman measurement was performed at two points: the center and the position away from the edge by 2 mm in the same way as in Example 1. It should be noted that when Raman-scattered light peaks of SiC were measured, the focal depth of an incident laser beam of a Raman spectrometer was adjusted to be a depth of about 10 µm from the wafer surface. When the focal depth is smaller than the above-mentioned value, a correct Raman shift value cannot be obtained due to the strain (disturbance of an atomic structure) caused by slicing. Further, when the focal depth is larger than the above-mentioned value, Raman-scattered light is absorbed by SiC, and hence sufficient signal intensity is not obtained.

After that, while the polishing processing of the wafer was performed successively, a Raman index was measured every time one step was completed (for example, at a finished point of lapping). That is, in general, a sliced wafer is subjected to lapping for removing the unevenness of the slice, diamond polishing for increasing the smoothness of the surface, and further chemical mechanical polishing (CMP) for removing processing strain on the wafer surface. In this example of the present invention, while the process similar to the foregoing was performed, a Raman index was measured every time each step was completed. Specifically, the procedure was as follows: the lapping was performed with respect to both the surfaces through use of diamond abrasive grains each having a size of from 10 µm to 1 µm for from 1 hour to several hours; the diamond polishing was performed through use of diamond abrasive grains each having a diameter of from 1 µm to 0.1 µm for from 3 hours to 5 hours; and the chemical mechanical polishing (CMP) was performed through use of a commercially available slurry dedicated for SiC for from 7 hours to 10 hours.

The tendency was observed in which the Raman index of the wafer became slightly smaller during a period of time from cutting to the completion of the CMP. The reason for this is considered as follows: the wafer became thin to decrease the stiffness thereof, and as a result, the wafer was deformed (warped) in a direction of relieving the internal stress. However, this change was small enough to be hidden in an error in one wafer and was not clear. That is, the Raman index is almost constant in any stage of the polishing step and can be used as a common indicator for the internal stress.

As the final finish of the wafer, the C surface is subjected to the CMP, and the Si surface is subjected to the diamond polishing. The finished thickness is 350 µm. In the completed wafer, the Si surface subjected to the CMP had a surface roughness Ra of from 0.05 nm to 0.15 nm, and the C surface subjected to the diamond polishing had a surface roughness Ra of about from 0.2 nm to 1.0 nm. The warpage was measured through use of Tropel manufactured by Corning Tropel Inc., and the SORI of a region excluding a 2-mm edge exclusion region was defined as the warpage of the substrate.

Figure 4:
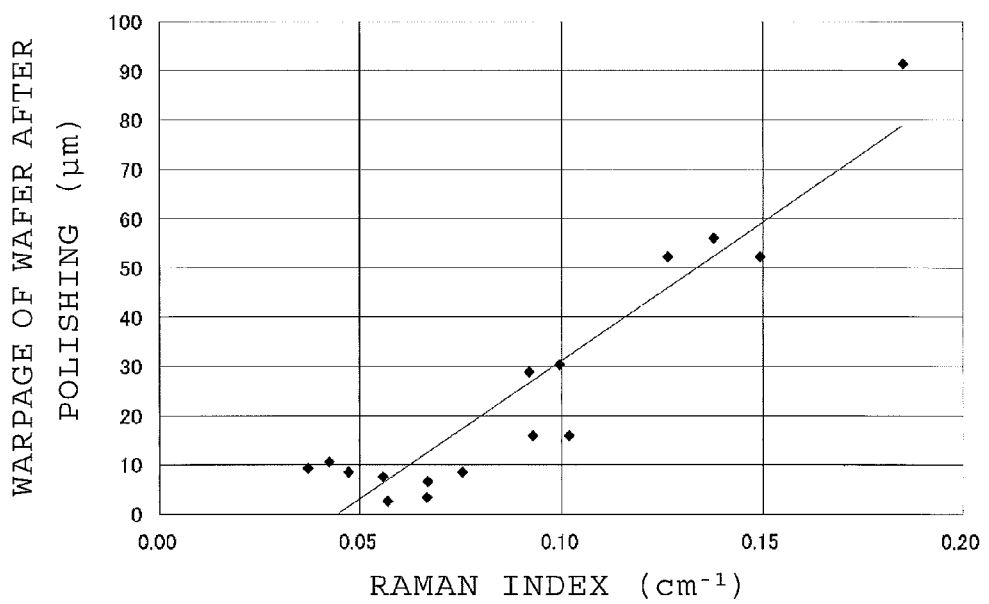
FIG. 4 is a graph for showing a relationship between a Raman index and warpage.
Figure 5A:
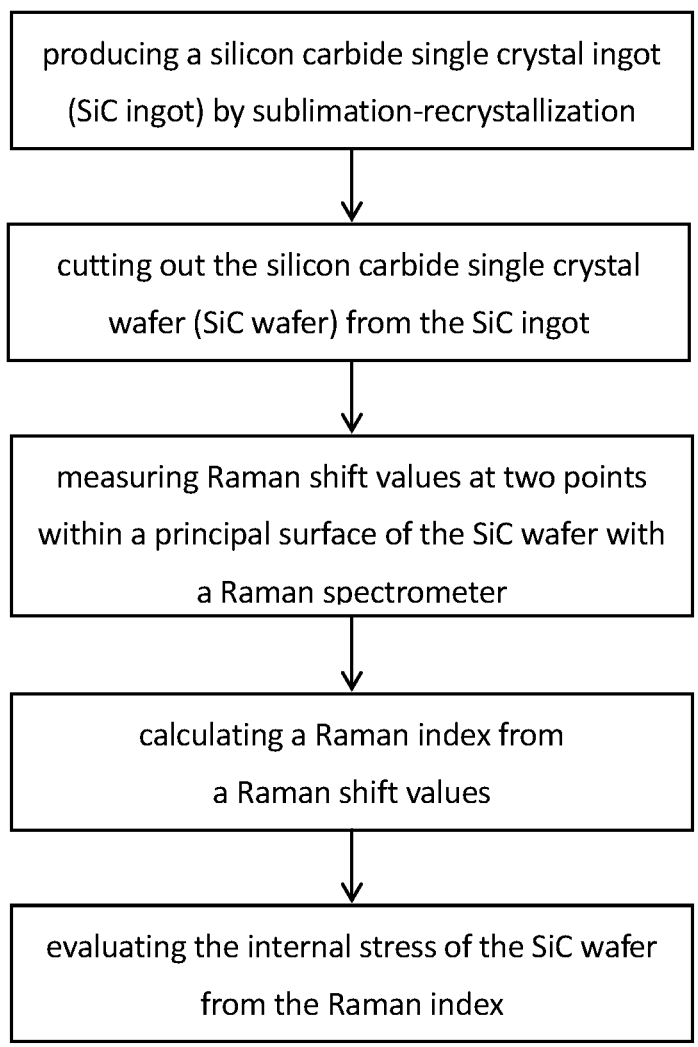
FIG. 5A is a process flow chart showing the steps of the inventive method of evaluating internal stress using a difference in Raman shift values.
Figure 5B:
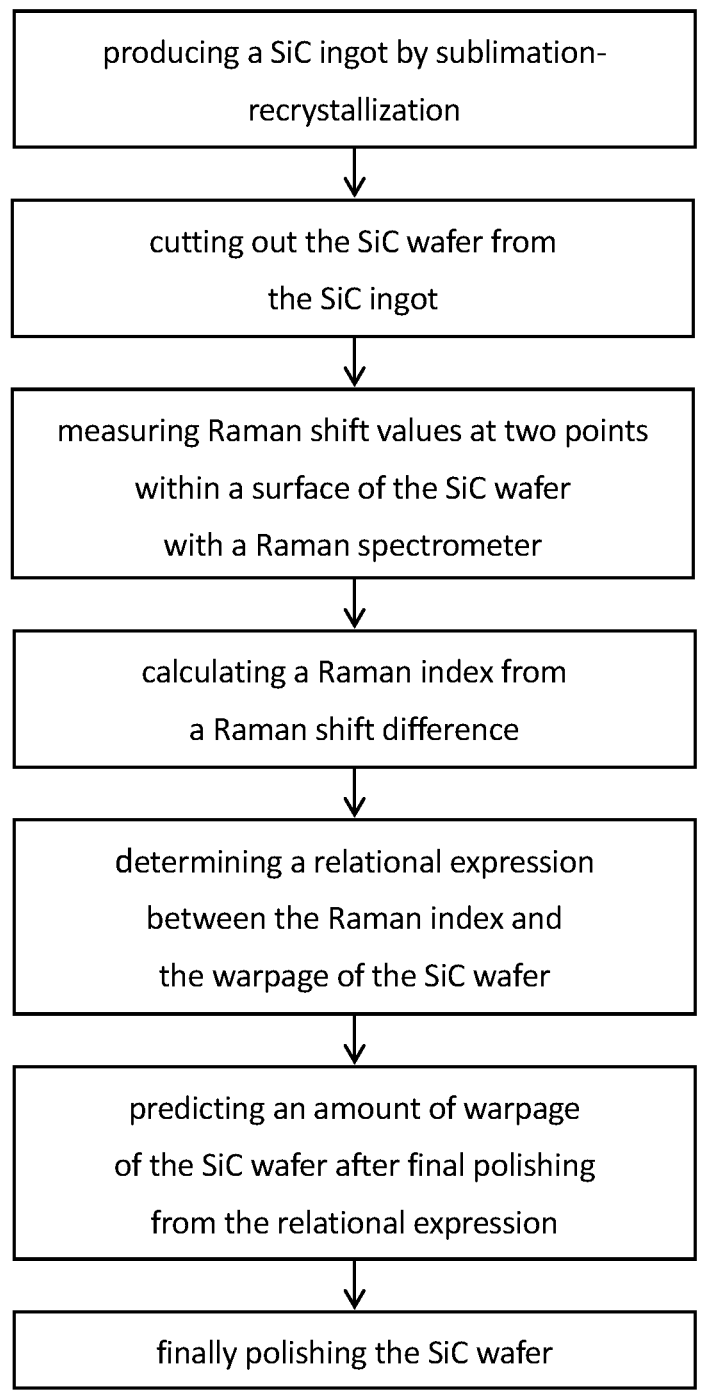
FIG. 5B is a process flow chart showing the steps of the inventive method of predicting warpage using a difference in Raman shift values.

In FIG. 4, data on the above-mentioned sixteen wafers is plotted, with the vertical axis representing the warpage of the wafer (product wafer) after the completion of polishing under the above-mentioned conditions and the horizontal axis representing the Raman index of the cut wafer (single crystal thin plate). When the Raman index and the warpage value were subjected to linear approximation by a least-square method, "Y (warpage)=561×(Raman index)−25" was obtained. The coefficient of determination was 0.873, and thus a satisfactory correlation was obtained.

Further, the polishing specifications of a total of four kinds were investigated in the same way as above except that the kind of the final polishing of the front and back surfaces (Si surface, C surface) and the thickness of the product wafer were changed. The results are shown in Table 2. Also in this case, the linear correlation was observed between the Raman index and the warpage, and the coefficient of determination was also satisfactory, i.e., 0.8 or more.

TABLE 2

| Finished thickness | Final polishing specifications | | Relational expression between warpage and Raman index | Coefficient of determination of left expression |
|---|---|---|---|---|
|  | Si surface | C surface |  |  |
| 350 µm | CMP | Diamond polishing | Y = 561X − 25 . . . (1) | 0.873 |
| 350 µm | CMP | Lapping | Y = 333X − 17 . . . (2) | 0.812 |
| 300 µm | CMP | Diamond polishing | Y = 750X + 10 . . . (3) | 0.849 |
| 250 µm | CMP | Diamond polishing | Y = 1670X + 16 . . . (4) | 0.823 |

Example 3

In Example 3, the warpage of a wafer was predicted through use of the relational expression between the warpage and the Raman index obtained in Example 2, and then the warpage was actually measured after polishing was actually performed.

First, seven cut wafers were randomly sampled for Example 3 from sixty-four cut wafers (single crystal thin plates) each having a thickness of 0.5 mm cut from a plurality of SiC single crystal ingots obtained by a sublimation-recrystallization method and measured for a Raman index in the same way as above. That is, the measurement was performed in two portions: the center and the position away from the edge by 2 mm in the same way as in Example 1, and the Si surface was measured. The results are shown in Table 3.

TABLE 3

| Wafer No. | Raman shift of center (cm$^{-1}$) | Raman shift of outer periphery (cm$^{-1}$) | Raman index |
|---|---|---|---|
| 31 | 776.4518 | 776.3499 | 0.1019 |
| 32 | 776.8073 | 776.7388 | 0.0685 |
| 33 | 776.6738 | 776.6189 | 0.0549 |
| 34 | 776.6395 | 776.5828 | 0.0567 |
| 35 | 776.7424 | 776.6483 | 0.0941 |
| 36 | 776.6432 | 776.5875 | 0.0557 |
| 37 | 776.6838 | 776.5875 | 0.0963 |

Next, the polishing specifications of each wafer were determined based on the Raman index of Table 3. First, wafer No. 31 had the largest Raman index among the seven cut wafers. Therefore, the specifications in which the predicted value became smallest were determined: CMP for the Si surface, lapping for the C surface, and the thickness of 350 μm. The predicted value of the warpage in this case is 17 μm based on Expression (2) shown in Table 2, which is a value satisfying a required value (40 μm or less) of the warpage in the specifications. Next, wafer Nos. 33 and 34 respectively had the smallest Raman index and the third smallest Raman index among the seven cut wafers. Therefore, the wafer Nos. 33 and 34 were classified into the specifications in which the warpage was likely to increase: CMP for the Si surface, diamond polishing for the C surface, and the thickness of 300 μm. The predicted value of the warpage in this case is 51 μm in the wafer No. 33 and 52 μm in the wafer No. 34 (both based on Expression (3) shown in Table 2). The predicted values were less than the general required value (60 μm or less) in the same specifications, and hence the wafer Nos. 33 and 34 were predicted to be able to be formed into products.

The Raman index of wafer No. 35 is significantly different from that of wafer No. 36. Regarding those wafers, based on the predicted values of the warpage and the required specifications, the specifications in which the warpage was most likely to increase among the currently investigated four polishing specifications were determined: CMP for the Si surface, diamond polishing for the C surface, and the thickness of 250 μm. The predicted value of the warpage of the wafer No. 35 was 173 μm, and hence it was predicted that the wafer No. 35 was able to be loaded onto a device line having a loose warpage reference (200 μm or less) in which wafers of the same polishing specifications were to be loaded. On the other hand, the predicted value of the wafer No. 36 was 109 μm, and hence it was predicted that the wafer No. 36 was able to be loaded onto a device line having a strict warpage reference (150 μm or less) in which wafers having the same polishing specifications were to be loaded. (Both the predicted values are based on Expression (4) shown in Table 2).

Regarding the other wafers, i.e., wafer Nos. 32 and 37, the specifications were determined: CMP for the Si surface, diamond polishing for the C surface, and the thickness of 350 μm. The predicted values of the warpage were respectively 13 μm and 29 μm and considered to satisfy the required value (40 μm or less) of the warpage in the specifications (both the predicted values are based on Expression (1) shown in Table 2).

The polishing processing was actually performed in accordance with the above-mentioned classifications of the application. The predicted values of the warpage and the actually measured values of the warpage after polishing are shown together in Table 4.

TABLE 4

| Wafer No. | Raman index | Polishing specifications (Si surface/C surface/finished thickness) | Predicted value of warpage | Actually measured value of warpage |
|---|---|---|---|---|
| 31 | 0.1019 | Si surface: CMP<br>C surface: lapping<br>Thickness: 350 μm | 17 μm | 21 μm |
| 32 | 0.0685 | Si surface: CMP<br>C surface: diamond polishing<br>Thickness: 350 μm | 13 μm | 9 μm |
| 33 | 0.0549 | Si surface: CMP<br>C surface: diamond polishing<br>Thickness: 300 μm | 51 μm | 50 μm |
| 34 | 0.0567 | Si surface: CMP<br>C surface: diamond polishing<br>Thickness: 300 μm | 52 μm | 49 μm |
| 35 | 0.0941 | Si surface CMP<br>C surface: diamond polishing<br>Thickness: 250 μm | 173 μm | 170 μm |
| 36 | 0.0557 | Si surface: CMP<br>C surface: diamond polishing<br>Thickness: 250 μm | 109 μm | 98 μm |
| 37 | 0.0963 | Si surface: CMP<br>C surface: diamond polishing<br>Thickness: 350 μm | 29 μm | 32 μm |

As shown in Table 4, the difference between the actually measured value of the warpage and the predicted value of the warpage was 11 μm at maximum, and thus it was shown that prediction was able to be performed with sufficiently high accuracy. All the seven wafers were able to realize the values satisfying the required values of the warpage in the respective specifications. On the other hand, for example, in the case where the wafer No. 31 is polished under the specifications: CMP for the Si surface, diamond polishing for the C surface, and the thickness of 300 μm, the predicted value of the warpage becomes 86 μm (predicted based on Expression (3) shown in Table 2). Similarly, in the case of the wafer No. 37, the predicted value of the warpage becomes 82 μm. Thus, both of the wafers fail due to the excessive warpage. When the technology of predicting the warpage of the present invention is used, optimum wafers can also be classified on the basis of the polishing specifications so that the warpage of a product wafer falls within a required value.

The invention claimed is:

1. A method of evaluating an internal stress of a silicon carbide single crystal wafer comprising:
   producing a silicon carbide single crystal ingot by sublimation-recrystallization;
   cutting out the silicon carbide single crystal wafer from the silicon carbide single crystal ingot;
   measuring Raman shift values at two points within a principal surface of the silicon carbide single crystal wafer with a Raman spectrometer;
   calculating a Raman index from the Raman shift values; and
   evaluating the internal stress of the silicon carbide single crystal wafer from the Raman index,
   wherein the measuring Raman shift values comprises:
   measuring a first Raman shift value (A) at a center of the silicon carbide single crystal wafer;

measuring a second Raman shift value (B) at an outer peripheral portion of the silicon carbide single crystal wafer; and calculating a Raman shift difference (A−B) between the first Raman shift value and second Raman shift value, wherein the Raman shift difference is the Raman index.

2. The method of claim 1, wherein the internal stress of the silicon carbide single crystal wafer is distributed in a concentric fashion.

3. A method of predicting warpage of a silicon carbide single crystal wafer comprising:

producing a silicon carbide single crystal ingot by sublimation-recrystallization;

cutting out the silicon carbide single crystal wafer from the silicon carbide single crystal ingot;

measuring Raman shift values at two points within any one of a front surface and a back surface of the silicon carbide single crystal wafer with a Raman spectrometer;

calculating a Raman index from a difference between the said Raman shift values;

determining a relational expression between the Raman index and the warpage of the silicon carbide single crystal wafer;

predicting an amount of warpage of the silicon carbide single crystal wafer after final polishing from the relational expression; and finally polishing the silicon carbide single crystal wafer;

wherein the predicting a warpage step is performed before the final polishing step.

4. The method of claim 3 wherein the cutting out the silicon carbide single crystal wafer from the silicon carbide single crystal ingot step comprises slicing the silicon carbide single crystal wafer from the silicon carbide single crystal ingot.

* * * * *